United States Patent
Köhler et al.

(10) Patent No.: US 9,765,012 B2
(45) Date of Patent: Sep. 19, 2017

(54) METHOD FOR PRODUCING DIARYL CARBONATE

(71) Applicant: Bayer MaterialScience AG, Leverkusen (DE)

(72) Inventors: Karl-Heinz Köhler, Aachen-Brand (DE); Henning Kahnis, Köln (DE); Johan Vanden Eynde, Zwijnaarde (BE); Gabriel Denecker, Kalmthout (BE); Ricarda Leiberich, Neu-Isenburg (DE); Kaspar Hallenberger, Leverkusen (DE); Korbinian Krämer, Köln (DE); Florian Lipski, Düsseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 50 days.

(21) Appl. No.: 14/653,629

(22) PCT Filed: Dec. 17, 2013

(86) PCT No.: PCT/EP2013/076787
§ 371 (c)(1),
(2) Date: Jun. 18, 2015

(87) PCT Pub. No.: WO2014/095776
PCT Pub. Date: Jun. 26, 2014

(65) Prior Publication Data
US 2016/0002143 A1    Jan. 7, 2016

(30) Foreign Application Priority Data
Dec. 18, 2012 (EP) ..................... 12197656

(51) Int. Cl.
C07C 68/02    (2006.01)

(52) U.S. Cl.
CPC .................. C07C 68/02 (2013.01)

(58) Field of Classification Search
CPC ................................................. C07C 68/02
See application file for complete search history.

(56) References Cited

U.S. PATENT DOCUMENTS

| | | | |
|---|---|---|---|
| 2,362,865 A | 11/1944 | Tryon et al. | |
| 2,837,555 A | 6/1958 | Lee | |
| 3,234,263 A | 2/1966 | Kurkjy et al. | |
| 4,012,406 A | 3/1977 | Buysch et al. | |
| 4,252,737 A | 2/1981 | Krimm et al. | |
| 4,330,665 A | 5/1982 | Krimm et al. | |
| 4,552,704 A | 11/1985 | Mark | |
| 4,554,110 A | 11/1985 | Mark | |
| 5,149,856 A | 9/1992 | Schön et al. | |
| 5,354,923 A | 10/1994 | Schön et al. | |
| 5,424,473 A * | 6/1995 | Galvan | C07C 68/02 558/260 |
| 9,150,490 B2 * | 10/2015 | Ooms | C07C 68/02 |
| 9,175,135 B2 * | 11/2015 | Ooms | C01B 7/04 |
| 2011/0278174 A1 * | 11/2011 | Ooms | C07C 68/02 205/349 |

FOREIGN PATENT DOCUMENTS

| | | | |
|---|---|---|---|
| DE | 2447348 A1 | 4/1976 | |
| DE | 34 45 552 A1 | 7/1985 | |
| DE | 34 45 555 A1 | 7/1985 | |
| DE | 40 06 520 A1 | 9/1991 | |
| DE | 40 36 594 A1 | 5/1992 | |
| EP | 000879 A1 | 3/1979 | |
| EP | 000880 A1 | 3/1979 | |
| EP | 039 452 A2 | 11/1981 | |
| EP | 0338760 A2 | 10/1989 | |
| EP | 0516355 A2 | 12/1992 | |
| EP | 2371806 A1 | 10/2011 | |
| FR | 2370784 A1 | 6/1978 | |
| JP | 4840573 A | 6/1973 | |
| JP | 5463023 A | 5/1979 | |
| JP | 54125617 A | 9/1979 | |
| JP | 57176932 A | 10/1982 | |
| JP | 61172852 A | 8/1986 | |
| JP | 0297092 A | 4/1990 | |
| JP | 0695219 | 4/1994 | |
| JP | 2001093560 A | 4/2001 | |
| JP | 2001093580 A | 4/2001 | |
| WO | WO-91/06526 A1 | 5/1991 | |

OTHER PUBLICATIONS

Kantarci et al. Process Biochemistry 2005, 40, 2263-2283.*
International Search Report for PCT/EP2013/076787 mailed Apr. 24, 2014.

* cited by examiner

*Primary Examiner* — Matthew Coughlin
(74) *Attorney, Agent, or Firm* — Drinker Biddle & Reath LLP

(57) ABSTRACT

The present application relates to a method for the continuous production of diaryl carbonate from phosgene and of at least one monohydroxy compound (monophenol) in the presence of catalysts, and to the use thereof for the production of polycarbonates.

10 Claims, 4 Drawing Sheets

METHOD FOR PRODUCING DIARYL CARBONATE

CROSS-REFERENCE TO RELATED APPLICATIONS

Figure 1:
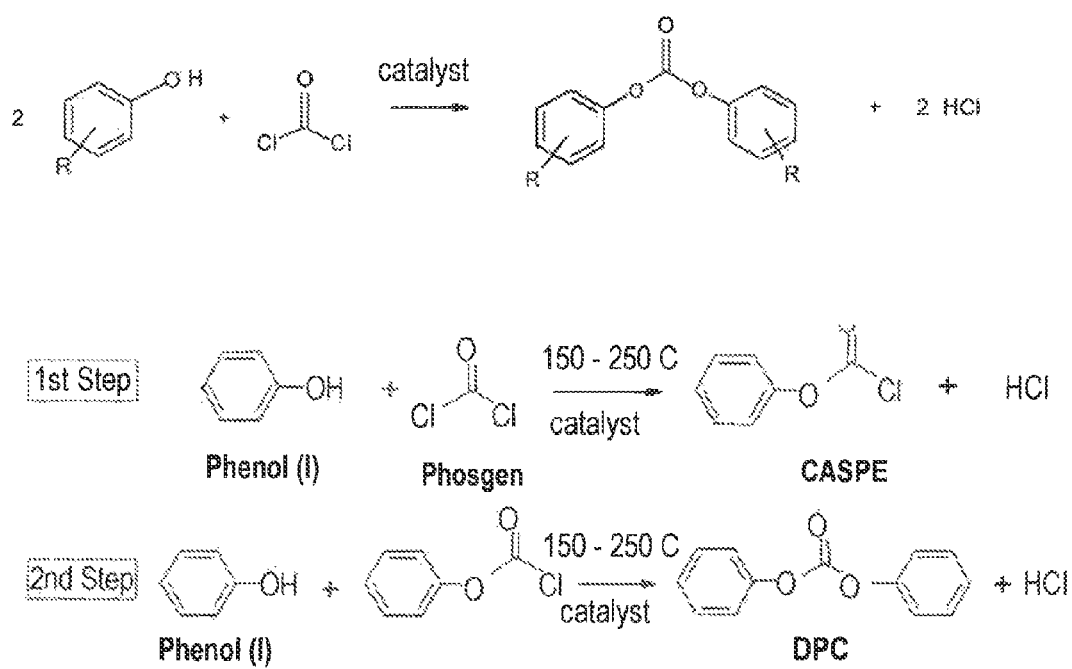

This application is a national stage application (under 35 U.S.C. §371) of PCT/EP2013/076787, filed Dec. 17, 2013, which claims benefit of European Application No. 12197656.7, filed Dec. 18, 2012.

The present application relates to a process for continuously preparing diaryl carbonate from phosgene and at least one monohydroxyl compound (monophenol) in the presence of catalysts, and to the use thereof for preparation of polycarbonates.

It is known that diaryl carbonate can be prepared by reacting an aromatic hydroxyl compound (monophenol) with a halogenated carbonyl. For example, processes for preparing a diaryl carbonate by reaction of an aromatic hydroxyl compound with phosgene in the presence of a solvent and sodium hydroxide as catalyst are common knowledge. The use of solvents and sodium hydroxide solution is disadvantageous here, since the aqueous alkali can cause partial hydrolysis of phosgene or chlorocarbonic esters, large amounts of sodium chloride are obtained as a by-product, and the solvent and catalyst have to be recovered.

For this reason, a process for preparing diaryl carbonate in the absence of solvent is of particular interest. Since no solvent is used, it need not be recycled either. If an aromatic hydroxyl compound, moreover, is reacted directly with phosgene, hydrogen chloride (HCl) forms as a by-product rather than sodium chloride. Accordingly, the recycling of the by-product (HCl) can be simplified, since discharge of the halides is distinctly reduced here, and the wastewater processing is distinctly simplified.

The preparation of diaryl carbonates and especially diphenyl carbonate by reaction of monophenols and phosgene without alkali and without use of solvents in the presence of a catalyst and by the direct phosgenation process have been examined and described in principle in the literature. See FIG. 1.

The reaction, for example, of phenol with phosgene first forms the phenyl chloroformate (PCF) intermediate and HCl in the first reaction step. PCF then reacts with a further phenol molecule to give DPC and a further HCl molecule.

Proposals for processes without solvents with soluble catalysts are described in U.S. Pat. Nos. 2,837,555, 3,234,263 and 2,362,865.

In this regard, there are therefore proposals to conduct a direct reaction of aromatic hydroxyl compounds with a halogenated carbonyl in the gas phase. However, this has disadvantages since these reactions are usually conducted at high temperatures and/or in partial vacuum.

A further approach is a binary gas/liquid phase reaction, as disclosed in DE 2447348 C2. In this case, the aromatic hydroxyl compound is generally used as the liquid phase. For maximum enhancement of efficiency, the halogenated carbonyl has to be converted to a maximum degree. In order to achieve this, the aromatic hydroxyl compound is used in excess relative to the halogenated carbonyl. This means, however, that there is an elevated recycling demand for the aromatic hydroxyl compound.

Therefore, there is a distinct preference for use of the aromatic hydroxyl compound with the halogenated carbonyl in almost equimolar amounts. However, in the case of almost equimolar use, there is an unfavorable effect on the equilibrium, which means that the conversion by known methods is inadequate and therefore the process is of low economic viability. Moreover, the hydrogen chloride which forms as a by-product during the reaction can distinctly reduce the concentration of halogenated carbonyl, and therefore likewise has an adverse effect on the conversion.

In view of the abovementioned disadvantages, there is a need for an improved process regime for preparation of diaryl carbonate.

In view of the prior art outlined above, it is an object of the present invention to provide a diaryl carbonate preparation process which gives products in high purity and good yield and enables simplified recycling of by-products which originate from polycarbonate production.

As already described, however, it is a problem that a direct reaction of an aromatic hydroxyl compound with a halogenated carbonyl in the gas phase or gas/liquid phase forms relatively large amounts of gas (for example phosgene or hydrogen chloride).

The present invention offers a solution to the abovementioned problems.

A further object to be achieved is that of increasing phosgene solubility and hence of enabling liquid entry into the reactor. The higher phosgene concentration in the liquid phase that results from the elevated phosgene solubility gives an improved phosgene conversion.

The present invention accordingly relates to a process for preparing a diaryl carbonate which does not have the aforementioned disadvantages.

The present invention accordingly provides a process for preparing diaryl carbonates proceeding from monophenols and carbonyl dihalide, which is characterized in that said reaction takes place under pressure and therefore the phosgene is present in high concentration in the liquid phase. The phosgene solubility is significantly increased by the elevated pressure, in contrast to the HCl solubility, which rises only insignificantly. Accordingly, the chemical equilibrium is not adversely affected by the elevated pressure, in contrast to higher G/A ratios.

Through the reaction of an aromatic hydroxyl compound and a halogenated carbonyl under pressure, it was therefore surprisingly possible to solve the abovementioned problems when the following equation is observed:

$$G/A < 0.010 \text{ [m/sec]},$$

where G is the entry volume flow rate of the liquid or dissolved halogenated carbonyl which is passed into the reactor, in $[m^3/sec]$, and A is the internal cross-sectional area orthogonal to the longitudinal axis in $[m^2]$, and where the ratio of the two parameters is also referred to as superficial velocity.

More preferably, $G/A < 0.0095$ [m/sec], even more preferably $< 0.0090$ [m/sec], especially preferably 0.0075 [m/sec], but preferably at least 0.0005 [m/sec].

Figure 5:
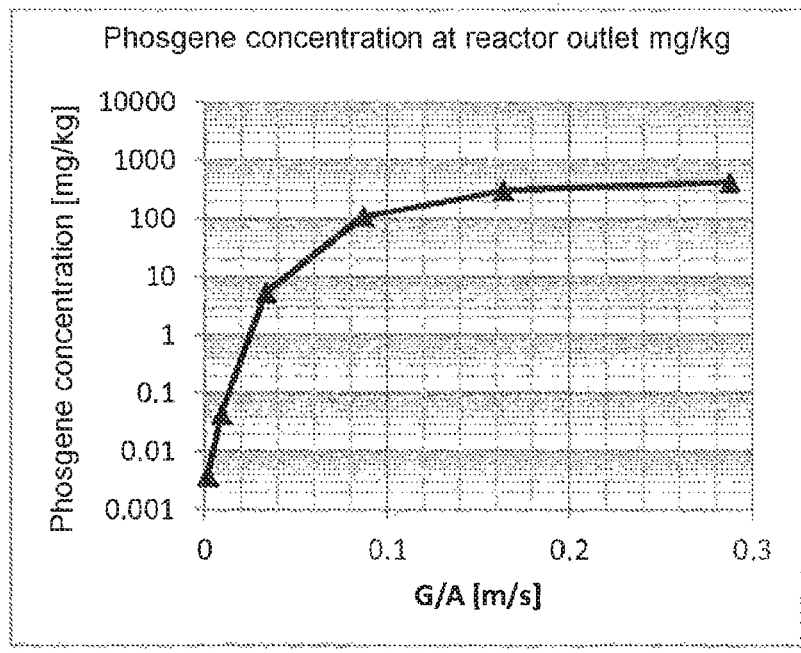

The improved phosgene conversion has been shown in tab. 2 and FIG. 5 by the graph of the phosgene concentration in the reactor outlet. It is apparent that, specifically below a G/A ratio of 0.010 [m/sec], especially below 0.009 [m/sec], the phosgene conversion rises exponentially once again, which was not to be expected.

Preferably, the different components in the system are mainly in liquid form. In addition, the following equation is regarded as advantageous:

$$H/D \geq 2$$

where H, for an illustrative upright cylindrical reactor (reaction column, bubble column), is the height of the liquid phase in the reactor in the gas-free state from the bottom end of the reactor to the upper edge of the liquid phase, and D is the diameter of the reactor.

More preferably, both the aromatic hydroxyl compound and halogenated carbonyl are passed into the reactor in the liquid phase.

Preferably, the aromatic hydroxyl compound and the halogenated carbonyl are introduced at the lower end of the reactor.

The preferred embodiment of the reactor takes the form of a bubble column. The reactor in the form of a bubble column is characterized by a ratio of height H of the liquid phase in the reactor in the gas-free state from the bottom end of the reactor to the upper edge of the liquid phase to diameter D, H/D, =2-80, preferably 2-50, more preferably 6-20. The premixed reactants are preferably fed into the reactor in liquid form at the lower end of the bubble column, which results in an upward flow through the reactor. The inventive bubble column reactor is used for reactions with evolution of gas. Limited solubility of the gas formed by the reaction results in formation of a gas phase over the reactor length. Preferably, the bubble column reactor used has an overflow in the upper section, which separates the liquid phase from the gas phase. The gas phase is removed at the top of the reactor. Preference is given here to observing the ratio between the distance of the middle of the overflow tube from the top of the reactor L and the reactor diameter D of L/D≥1. Other constructions, for example annular overflows or expansions of the top diameter to reduce droplet entrainment in the gas phase can be found in the prior art, as can bubble separators which can be connected downstream of said overflow tube in order to prevent entrainment of gas in the liquid. The reactor may be executed as a pure bubble column or with internals such as random packings, structured packings, or preferably segmented internals, for example perforated sheets. The choice of perforated sheet geometries (hole diameter, number of holes and resulting proportion of the clear area of the perforated sheets) and of the number of segments into which the reactor is divided is made according to the customary practical rules, in such a way that the residence time distribution of the liquid corresponds very substantially to that of a plug flow reactor and, at the same time, backup of the gas beneath the perforated plates is reduced to a minimum, in order to maximize the effective liquid volume and hence the liquid residence time in the reactor. More particularly, it may also be advisable to use different perforated plate geometries over the height of the reactor in accordance with the local formation of gas resulting from the progress of the reaction.

The above-described bubble column reactor is used for the direct phosgenation of aromatic hydroxyl compounds, preferably for the direct phosgenation of phenol to diphenyl carbonate and HCl. The reaction is preferably run under pressures of 3-100 bar, more preferably 12-25 bar, and at temperatures of preferably 120-220° C., more preferably 170-200° C. Preferably, the reaction in the bubble column reactor takes place in the absence of a solvent, more preferably in the melt.

For the reaction, the homogeneous catalyst used is preferably pyridine or pyridine*HCl and more preferably $TiCl_4$ or $Ti(OPh)_4$ or $AlCl_3$. The liquid residence time is preferably 0.5-4 h, more preferably 0.5-2 h./ Alternatively, the bubble column may also be divided in the form of a cascade of bubble columns, in which case the residence time per bubble column is reduced correspondingly. The mixture of phenol, liquid or dissolved phosgene and the homogeneous catalyst used is combined in a suitable mixing nozzle and fed to the reactor from the bottom in upward flow. The mixing of said components can also be effected in the reactor itself; for this purpose, the reactor may be equipped, for example, in the lower entry region with static or active mixing elements known from the prior art. The reactor may be insulated in a suitable manner for the preferred adiabatic mode of operation.

Figure 2:
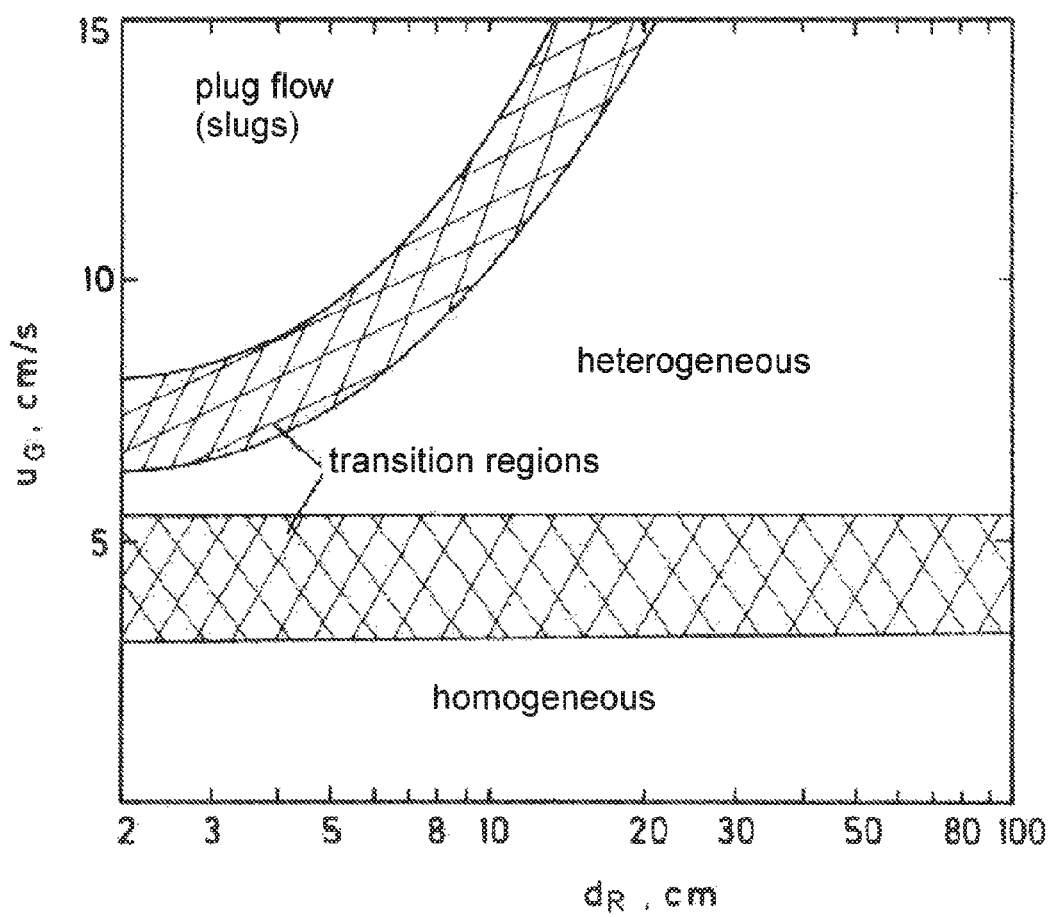

By virtue of the gas phase which arises during the reaction and is only of limited solubility in the reaction mixture, a homogeneous flow regime according to FIG. 2 preferably develops in the reactor. The reactor design is conducted so as to result preferably in a superficial gas velocity at the reactor outlet of 1-5 cm/s, more preferably of 2-3 cm/s, such that there is only very limited backmixing. The total proportion of the gas phase in the bubble column reactor, according to the invention, is preferably between 10% and 20%. Alternatively, the reactor can also be operated in a heterogeneous flow regime at gas velocities above the values mentioned; in that case, to preserve the liquid residence time distribution in accordance with plug flow, it may be advantageous to equip the reactor with segmenting internals, for example perforated sheets, in the manner explained above.

The reactor is operated in such a way that the molar ratio of phenol to phosgene at the reactor inlet is between 5:1 and 2:1, more preferably between 3:1 and 2.2:1. At the reactor outlet, the phosgene content is preferably <1%, more preferably <10 ppm, and the PCF content is preferably <1%, more preferably <100 ppm. Compare FIG. 4.

In the process for direct phosgenation of phenol to diphenyl carbonate and HCl which is to be conducted, the bubble column reactor is used in one stage, preferably in a cascaded design with two stages. Alternatively, it is also possible to use more than two stages in a cascaded design. In the preferred case, the first reaction stage is operated under pressures of 3-100 bar, more preferably 12-25 bar, at temperatures of preferably 120-220° C., more preferably 170-200° C. The residence time in the first stage is preferably 0.5-4 h, more preferably 0.5-2 h. The mixture of phenol, liquid phosgene and the homogeneous catalyst used is combined in a suitable mixing nozzle and fed to the reactor from the bottom in upward flow. The reactor may be insulated in a suitable manner for the preferred adiabatic mode of operation.

The reactor is operated in such a way that the molar ratio of phenol to phosgene at the reactor inlet is between 5:1 and 2:1, more preferably between 3:1 and 2.2:1. At the reactor outlet, the phosgene content in the liquid phase is preferably <1%, more preferably <200 ppm and especially <100 ppm. Compare FIG. 4. In the gas phase, the phosgene content is preferably <1%, more preferably <2000 ppm.

The second reaction stage, in the preferred case, is operated under pressures of 3-100 bar, more preferably 12-25 bar, at temperatures of preferably 120-220° C., more preferably 200-210° C. The residence time is preferably 0.2-4 h, more preferably 0.2-2 h. Alternatively, the bubble column may also be divided in the form of a cascade of bubble columns, in which case the residence time per bubble column is reduced correspondingly. The mixture which originates from the first reaction stage, of mainly phenol, DPC and PCF and the homogeneous catalyst used, is preheated to the reaction temperature and fed to the second reaction stage from below in upward flow. The reactor may be insulated in a suitable manner for the preferred adiabatic mode of operation.

By virtue of the gas phase which arises during the reaction and is only of limited solubility in the reaction mixture, a homogeneous flow regime according to FIG. 2 preferably develops in the reactor. The reactor design is conducted so as to result preferably in a superficial gas velocity at the reactor outlet of 1-5 cm/s, more preferably of 2-3 cm/s, such that there is only very limited backmixing. The total proportion of the gas phase in the bubble column reactor, according to the invention, is between 5% and 35%.

The reactor is operated in such a way that the phosgene content in the liquid phase at the reactor outlet of the second stage is preferably <100 ppm, more preferably <10 ppm, and the PFC content is preferably <2000 ppm, more preferably <100 ppm. In the gas phase, the phosgene content is preferably <25 ppm.

The HCl which forms can subsequently, after suitable purification if required, be converted back to chlorine either by electrolysis, preferably membrane electrolysis, optionally with the aid of an oxygen-depolarized cathode, or a thermal oxidation in the presence of oxygen and a suitable catalyst (Deacon process), and this chlorine can be reused in turn for preparation of phosgene by reaction with carbon monoxide. This phosgene is then preferably used at least partly for reaction with a monophenol, in order to prepare the diaryl carbonate.

Diaryl carbonates prepared in the context of the invention are preferably those of the general formula (I)

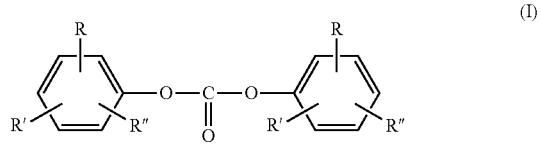

where R, R' and R" are each independently H, linear or branched, optionally substituted C1-C34-alkyl, preferably C1-C6-alkyl, more preferably C1-C4-alkyl, C1-C34-alkoxy, preferably C1-C6-alkoxy, more preferably C1-C4-alkoxy, C5-C34-cycloalkyl, C7-C34-alkylaryl, C6-C34-aryl or a halogen radical, preferably a chlorine radical, and R, R' and R" on both sides of the formula (I) may be the same or different. R may also be —COO—R''' where R∝1'may be H, optionally branched C1-C34 alkyl, preferably C1-C6-alkyl, more preferably C1-C4-alkyl, C1-C34-alkoxy, preferably C1-C6-alkoxy, more preferably C1-C4-alkoxy, C5-C34-cycloalkyl, C7-C34-alkylaryl or C6-C34-aryl. Preferably, R, R' and R" on both sides of the formula (I) are the same. Most preferably, R, R' and R" are each H.

Diaryl carbonates of the general formula (I) are, for example: diphenyl carbonate, methylphenyl phenyl carbonates and di(rnethylphenyl) carbonates, also as a mixture, where the position of the methyl group on the phenyl rings may be as desired, and also dimethylphenyl phenyl carbonates and di(dimethylphenyl) carbonates, also as a mixture, where the position of the methyl groups on the phenyl rings may be as desired, chlorophenyl phenyl carbonates and di(chlorophenyl) carbonates, where the position of the methyl group on the phenyl rings may be as desired, 4-ethylphenyl phenyl carbonate, di(4-ethylphenyl) carbonate, 4-n-propylphenyl phenyl carbonate, di(4-n-propylphenyl) carbonate, 4-isopropylphenyl phenyl carbonate, di(4-isopropylphenyl) carbonate, 4-n-butylphenyl phenyl carbonate, di(4-n-butylphenyl) carbonate, 4-isobutylphenyl phenyl carbonate, di(4-isobutylphenyl) carbonate, 4-tert-butylphenyl phenyl carbonate, di(4-tert-butylphenyi) carbonate, 4-n-pentylphenyl phenyl carbonate, di(4-n-pentylphenyl) carbonate, 4-n-hexylphenyl phenyl carbonate, di(4-n-hexylphenyl) carbonate, 4-isooctylphenyl phenyl carbonate, di(4-isooctylphenyl) carbonate, 4-n-nonylphenyl phenyl carbonate, di(4-n-nonylphenyl) carbonate, 4-cyclohexylphenyl phenyl carbonate, di(4-cyclohexylphenyl) carbonate, 4-(1-methyl-1-phenylethyl)phenyl phenyl carbonate, di[4-(1-methyl-1-phenylethyl)phenyl]carbonate, biphenyl-4-yl phenyl carbonate, di(biphenyl-4-yl) carbonate, 1-naphthyl phenyl carbonate, 2-naphthyl phenyl carbonate, di(1-naphthyl) carbonate, di(2-naphthyl) carbonate, 4-(1-naphthyl)phenyl phenyl carbonate, 4-(2-naphthyl)phenyl phenyl carbonate, di[4-(1-naphthyl)phenyl]carbonate, di[4-(2-naphthyl)phenyl]carbonate, 4-phenoxyphenyl phenyl carbonate, di(4-phenoxyphenyl) carbonate, 3-pentadecylphenyl phenyl carbonate, di(3-pentadecylpbenyl) carbonate, 4-tritylphenyl phenyl carbonate, di(4-tritylphenyl) carbonate, (methyl salicylate) phenyl carbonate, di(methyl salicylate) carbonate, (ethyl salicylate) phenyl carbonate, diethyl salicylate) carbonate, (n-propyl salicylate) phenyl carbonate, di(n-propyl salicylate) carbonate, (isopropyl salicylate) phenyl carbonate, di(isopropyl salicylate) carbonate, (n-butyl salicylate) phenyl carbonate, di(n-butyl salicylate) carbonate, (isobutyl salicylate) phenyl carbonate, di(isobutyl salicylate) carbonate, (tert-butyl salicylate) phenyl carbonate, di(tert-butyl salicylate) carbonate, di(phenyl salicylate) carbonate and di(benzyl salicylate) carbonate.

Preferred diaryl carbonates are: diphenyl carbonate, 4-tert-butylphenyl phenyl carbonate, di(1-tert-butylphenyl) carbonate, biphenyl-4-yl phenyl carbonate, di(biphenyl-4-yl) carbonate, 4-(1-methyl-1-phenylethyl)phenyl phenyl carbonate and di[4-(1-methyl-1-phenylethyl)phenyl]carbonate.

Particular preference is given to diphenyl carbonate.

In the context of the invention, suitable aromatic hydroxyl compounds are preferably those of the general formula (III)

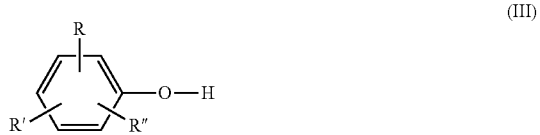

in which R, R' and R" may each independently be as defined for the general formula (I).

Such aromatic hydroxyl compounds are, for example: phenol, o-, m- or p-cresol, also as a mixture of the cresols, dimethylphenol, also as a mixture, where the position of the methyl groups on the phenol ring may be as desired, e.g. 2,4-, 2,6-, or 3,4-dimethylphenol o-, m- or p-chlorophenol, o-, m- p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, or p-methoxyphenol, 4-cyclohexylphenol, 4-(1-methyl-1-phenylethyl)phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicylic acid, isopropylsalicylic acid, n-butylsalicylic acid, isobutylsalicylic acid, tert-butylsalicylic acid, phenylsalicylic acid and benzylsalicylic acid.

Preferred aromatic hydroxyl compounds are phenol, 4-tert-butylphenol, biphenyl-4-ol and 4-(1-methyl-1-phenylethyl)phenol.

Particular preference is given to phenol.

For the reaction steps which occur in the first reaction column, it is possible to use transesterification catalysts known from the literature. These are transesterification catalysts known from the literature for the dialkyl carbonate/phenol transesterification, for example $AlX_3$, $TiX_3$, $UX_4$, $TiX_4$, $VOX_3$, $VX_5$, $ZnX_2$, $FeX_3$, $PbX_2$ and $SnX_4$, in which X represents halogen, acetoxy, alkoxy or aryloxy radicals (DE-A 2 58 412). Particularly preferred usable catalysts are metal compounds such as $AlX_3$, $TiX_4$, $PbX_2$ and $SnX_4$, for example titanium tetrachloride, titanium tetramethoxide, titanium tetraphenoxide, titanium tetraethoxide, titanium tetraisopropoxide, titanium tetradodecoxide, tin tetraisooctoxide and aluminum triisopropoxide. Very particular preference is given to metal compounds $TiX_4$, especially $TiCl_4$. The metal compounds mentioned are used preferably in amounts of 0.001% to 5% by weight, preferably of 0.005% to 5% by weight and more preferably of 0.01% to 5% by weight, based on the weight of the reaction mixture to be converted. Preference is given to aluminum oxide, titanium oxide, zirconium oxide, calcium titanate, magnesium titanate and magnesium aluminum hydrotalcite, which are used in the novel process preferably in the form of a fixed bed, in a column with catalyst in the form of random packings or of a coating on structured packings (also conceivable in a bubble column is triphasic operation with suspended catalyst (slurry bubble column, liquid fluidized bed)), and to titanium chloride, zirconium chloride, aluminum chloride and titanium phenoxide, which are used in the four of homogeneous catalysts.

Further preferred catalysts are basic nitrogen-containing catalysts, especially quaternary ammonium salts, for example organic and inorganic salts such as tetramethylammonium and tetraethylammonium salts, in addition are likewise aromatic nitrogen-containing heterocyclic bases, for example pyridine, 2-methoxypyridine, 2-hydroxypyridine, quinoline, isoquinoline, picoline, acridine, imidazoles, 2-methylimidazole, benzimidazoles, pyrazole, pyrazine, pyrimidine, triazoles and benzotriazoles, and also the salts thereof, including organic and inorganic salts of the aforementioned aromatic nitrogen-containing heterocyclic bases. Furthermore, polymers of the aforementioned compounds, for example polyvinylpyridine, are likewise suitable catalysts. Preference is given to pyridine, α-picoline, mixed β- and γ-picolines, isoquinoline, 2-hydroxypyridine and imidazole. Particular preference is given to pyridine.

The amount of nitrogen-containing catalyst is preferably in the range from 0.1 to 10 mol %, preferably' from 0.5 to 5 mol %, in relation to the monophenol. The nitrogen-containing catalyst is converted rapidly to the corresponding hydrochloride in the reaction medium. Therefore, an equal catalyst activity is achieved when chlorides of the abovementioned compounds are used. However, it is likewise possible to use bromides, sulfates and nitrates, and also weak acids of the abovementioned compounds, for example formates, acetates or phosphates.

Particular preference is given to aluminum oxide, aluminum chloride and $TiCl_4$ or pyridine.

In the context of the invention, halogen is fluorine, chlorine or bromine, preferably fluorine or chlorine, more preferably chlorine.

Further usable catalysts are organotin compounds of the general formula $(R_{11})_4$—X—Sn(Y)X in which Y is an $OCOR_{12}$, OH or OR radical, where $R_{12}$ is $C_1$—$C_{12}$-alkyl, $C_6$-$C_{12}$-aryl or $C_7$-$C_{13}$-alkylaryl, $R_{11}$ is as defined for $R_{12}$ independently of $R_{12}$, and x is an integer from 1 to 3, dialkyltin compounds having 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctoxide, octyltin triisooctoxide, butylstannoic acid and octylstannoic acid, in amounts of 0.001% to 20% by weight (cf. EP 879 A, EP 880 A, EP 39 452 A, DE-A 34 45 555, JP 79/63023), polymeric tin compounds of the formula —[—$RR_{11}$Sn—O—]— in which R and $R_{11}$ are each independently as defined above for $R_{12}$, for example poly[oxy(dibutylstannylene)]poly[oxy(dioctylstannylene)], poly[oxy(butylphenylstannylene)] and poly[oxy(diphenylstannylene)] (DE-A 34 45 552), polymeric hydroxystannoxanes of the formula —[—RSn(OH)—O—]—, for example poly(ethylhydroxystannoxane), poly(butylhydroxystannoxane), poly-(octylhydroxystannoxane), poly(undecylhydroxystannoxane) and poly(dodecylhydroxystannoxanes), in amounts of 0.001% to 20% by weight, preferably of 0.005% to 5% by weight, based on dialkyl carbonate (DE-A 40 06 520). Further usable tin compounds are Sn(II) oxides of the general formula.

X—$R_2$Sn—O—$R_2$Sn—Y in which X and Y are each independently OH, SCN, $OR_{13}$, $OCOR_{13}$ or halogen and R is alkyl, aryl, in which $R_{13}$ is as defined above for $R_{12}$ (EP 0 338 760).

As further usable catalysts come lead compounds, optionally together with triorganophosphines, a chelate compound or an alkali metal halide, for example $Pb(OH)_2 2PbCO_3$, $Pb(OCOCH_3)_2$, $Pb(OCOCH_3)_2$ .2LiCl, $Pb(OCOCH_3)_2$.2PPh$_3$, in amounts of 0.001 to 1 mol, preferably of 0.005 to 0.25 mol, per mole of dialkyl carbonate (JP 57/176932, JP 01/093580), and also other lead(II) and lead(IV) compounds, such as PhO, $PbO_2$, minium, plumbites and plumbates (JP 01/093560), iron(III) acetate (JP 61/1 72 852), and also copper salts and/or metal complexes, for example of alkali metals, zinc, titanium and iron (JP 89/005588).

In addition, heterogeneous catalyst systems are usable in the processes. These are, for example, mixed oxides of silicon and titanium, which are obtainable by combined hydrolysis of silicon and titanium halides (JP 54/125617), or titanium dioxides with a high BET surface area of >20 m2/g (DE-A 40 36 594).

Further suitable catalysts are
a) activated carbons having surface areas of 200 to 3000 m2/g, determined by the BET method, which have been produced from sawdust and other wood wastes, straw, charcoal types, nutshells, mineral oil tars, lignin, polysaccharides, polyacrylonitrile, bones, peat or coke products formed from brown coal or hard coal, preferably from wood, cellulose, lignin, bituminous coal or brown coal, peat or hard coal coke.
b) aluminosilicates, selected from the group of the zeolites of the general formula

$M_{2/n}O$. x $SiO_2.Al_2O_3$. y $H_2O$ in which
M represents cations such as protons or metal cations of Mendeleev's Periodic Table of the Elements,
n is the valency of the cation,
x is the molar ratio $SiO_2.Al_2O_3$, where
x may be a number of 1.0-50.0, and
y is a number of 0-9.
or zeolite-like compounds such as ALPOs and SAPOs or sheet silicates of the kaolin, serpentine, montmorillonite or bentonite type, or pillared clays, or precipitated $SiO_2/Al_2O_3$ catalysts,
c) aluminas or γ-aluminas having surface areas determined by the BET method of 2 to 500 m$^2$/g, d) oxide(s) of metals of group IVB of the Periodic Table, for example oxides of titanium, zirconium or hafnium, having surface areas determined by the BET method of 2 to 500 m$^2$/g, e) metalates of the general formula $$A_xB_yO_z$$

in which
A is a mono-, di- and/or trivalent metal cation and
B is a tri-, tetra-, penta- and/or hexavalent metal cation and
x is a number from 1 to 4 and
y is a number of 1 or 2 and
z is a number of 3, 6, 7 or 9, f) hard materials having metal-like properties (ceramic precursors) of the general formula $$a_xB_yC_zD_w$$

in which
A is an element from groups 3 to 10, 13 and 14 of the Periodic System of the Elements (IUPAC notation) and
B is an element from groups 13, 14, 15 and 16 excluding oxygen,
C is an element from groups 14 and 15 and
D is an element from groups 14 and 15 and
x is a number from 1 to 4 and
y is a number from 1 to 4 and
z is a number from 0 to 4 and
w is a number from 0 to 4,
where A, B, C and D each conic from different groups or, in the case of the same group, from different periods, with the proviso that A is not aluminum when B is carbon and, at the same time, z and w are each 0, g) mixed hydroxides of the general formula (III)

$$[M(II)_{1-x} M(III)_x M(IV)_y (OH)_2]A^{n-}{}_{z/n}\cdot m\ H_2O(III),$$

in which
M(II) is a divalent metal cation and
M(III) is a trivalent metal cation and
M(IV) is a tetravalent metal cation and
x is a number from 0.1 to 0.5 and
y is a number from 0 to 0.5,
z is 1+y and
m is a number from 0 to 1,
A is an inorganic anion such as OH$^-$, NO$_3^-$, CO$_3^{2-}$, SO$_4^{2-}$, CrO$_4^{2-}$ or Cl$^-$,
n is 1 to 2, h) organophosphorus compounds, in homogeneous or optionally polymer-bound form.

Optionally, the homogeneous catalysts may be applied to an inert support, as described in JP 695219, WO 91/06526, U.S. Pat. No. 5,424,473 and EP 516 355.

The catalysts can be used individually or in conjunction with one another.

In a preferred embodiment, the catalyst is used in amounts of 0.5% to 100% by weight, based on the amount of monohydroxyl compound (monophenol), in a mode of operation which is not fully continuous, or with space velocities of 0.1 to 20 g of monohydroxyl compound (monophenol) per g of catalyst per hour in a fully continuous mode of operation. In another preferred embodiment, especially when the catalyst is TiCl$_4$ or Ti(OPh)$_4$, the catalyst can also be used with space velocities exceeding 20 g of monohydroxyl compound (monophenol) per g of catalyst per hour in fully continuous mode.

The catalyst is preferably introduced into the first reaction column in dissolved or suspended form together with the stream comprising the aromatic hydroxyl compound(s). Alternatively, the catalyst can also be metered in separately, for example, in an alcohol corresponding to the alkyl alcohol or a suitable inert solvent. In the case of use of heterogeneous catalysts, they can be used in a mixture with the random packings mentioned, in a suitable shape in place of random packings or as a bed on any column trays installed.

Dialkyl carbonates used in the context of the invention are preferably those of the general formula (IV)

where R1 and R2 are each independently linear or branched, optionally substituted C1-C34-alkyl, preferably C1-C6-alkyl, more preferably C1-C4-alkyl. R1 and R2 may be the same or different. Preferably, R1 and R2 are the same.

C1-C4-Alkyl in the context of the invention is, for example, methyl, ethyl, n-propyl, isopropyl, n-butyl, sec-butyl, tert-butyl; C1-C6-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2 -ethylbutyl, 1,1,2-trimethylpropyl, 1,2,2-trimethylpropyl, 1-ethyl-1 -methylpropyl, 1-ethyl-2-methylpropyl or 1-ethyl-2-methylpropyl; C1-C34-alkyl is additionally, for example, n-heptyl and n-octyl, pinacyl, adamarityl, the isomeric menthyls, n-nonyl, n-decyl, n-dodecyl, n-tridecyl, n-tetradecyl, n-hexadecyl or n-octadecyl. The same applies to the corresponding alkyl radical, for example in aralkyl or alkylaryl radicals. Alkylene radicals in the corresponding hydroxyalkyl or aralkyl or alkylaryl radicals are, for example, the alkylene radicals corresponding to the above alkyl radicals.

The above lists are illustrative and should not be understood as a limitation.

Preferred dialkyl carbonates are dimethyl carbonate, diethyl carbonate, di(n-propyl) carbonate, di(isopropyl) carbonate, di(n-butyl) carbonate, di(sec-butyl) carbonate, di(tert-butyl) carbonate or dihexyl carbonate. Particular preference is given to dimethyl carbonate or diethyl carbonate. Very particular preference is given to dimethyl carbonate.

The dialkyl carbonates are preferably prepared from cyclic alkylene carbonates having the formula (V):

where, in the formula, R3 and R4 may each independently be hydrogen, substituted or unsubstituted C1-C4-alkyl, substituted or unsubstituted C2-C4-alkenyl or substituted or unsubstituted C6-C12-aryl, and R3 and R4 together with the two three-membered ring carbon atoms may be a saturated carbocyclic ring having 5-8 ring members.

The cyclic alkylene carbonates are reacted with alcohols of the formula

R5—OH where R5 is a straight-chain or branched C1-C4-alkyl.

The halogenated carbonyl used is preferably phosgene or bromocarbonyl, but more preferably phosgene. It is possible to use one or more halogenated carbonyls.

The halogenated carbonyl may contain impurities, especially proportions of inert gases, for example nitrogen or argon, but the halogenated carbonyl preferably has a purity of at least 90% by weight, preferably at least 95% by weight, more preferably at least 99% by weight.

FIG. 1: Reaction mechanisms

FIG. 2: Flow regimes in bubble columns [Wolf-Dieter Deckwer: Reaktionstechnik in Blasensäulen [Reaction Methodology in Bubble Columns], Salle+Sauerländer, Frankfurt am Main, 1985, p. 184, FIG. 7.1]

Figure 3:
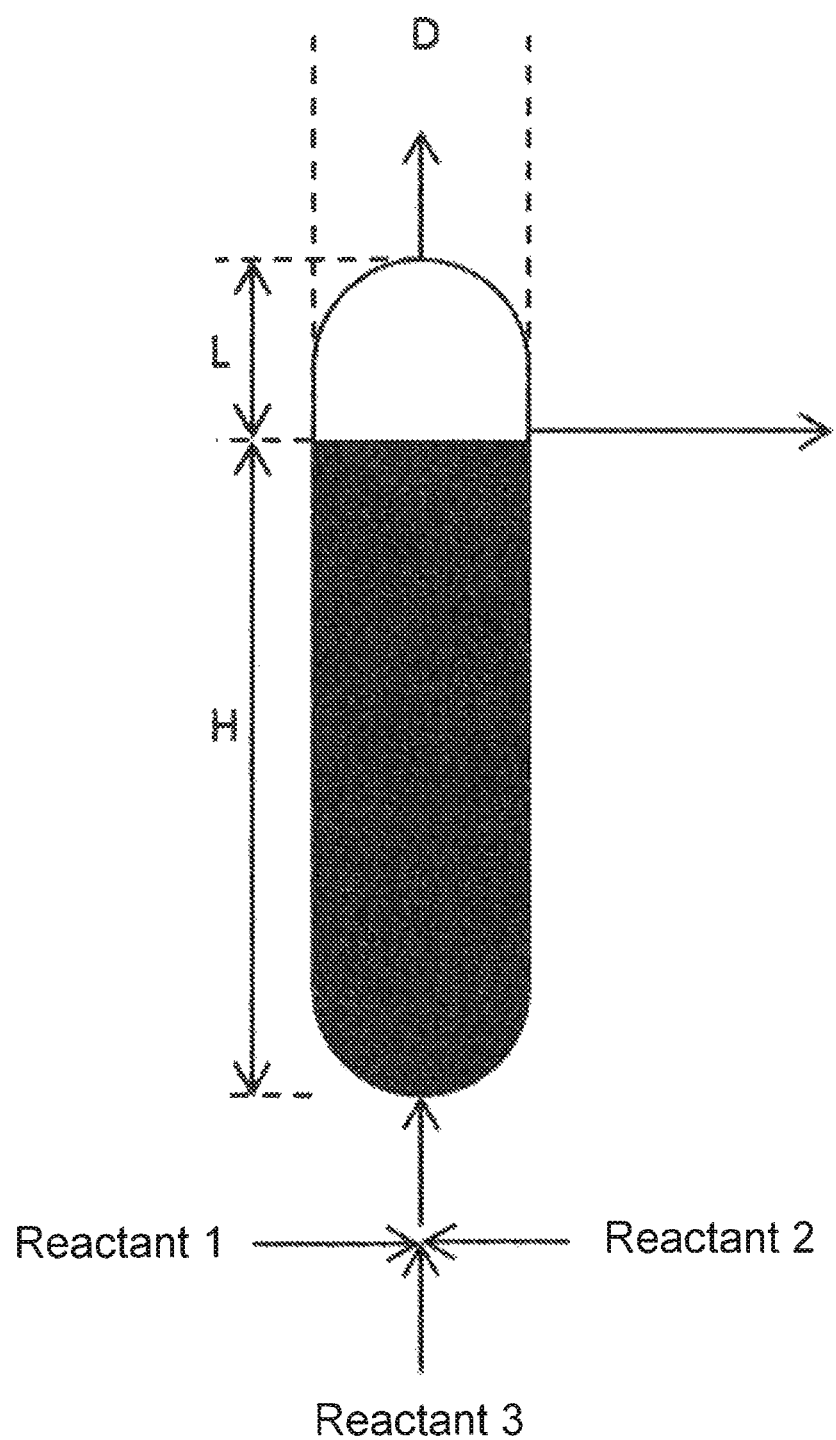

FIG. 3: Schematic diagram of a bubble column

Figure 4:
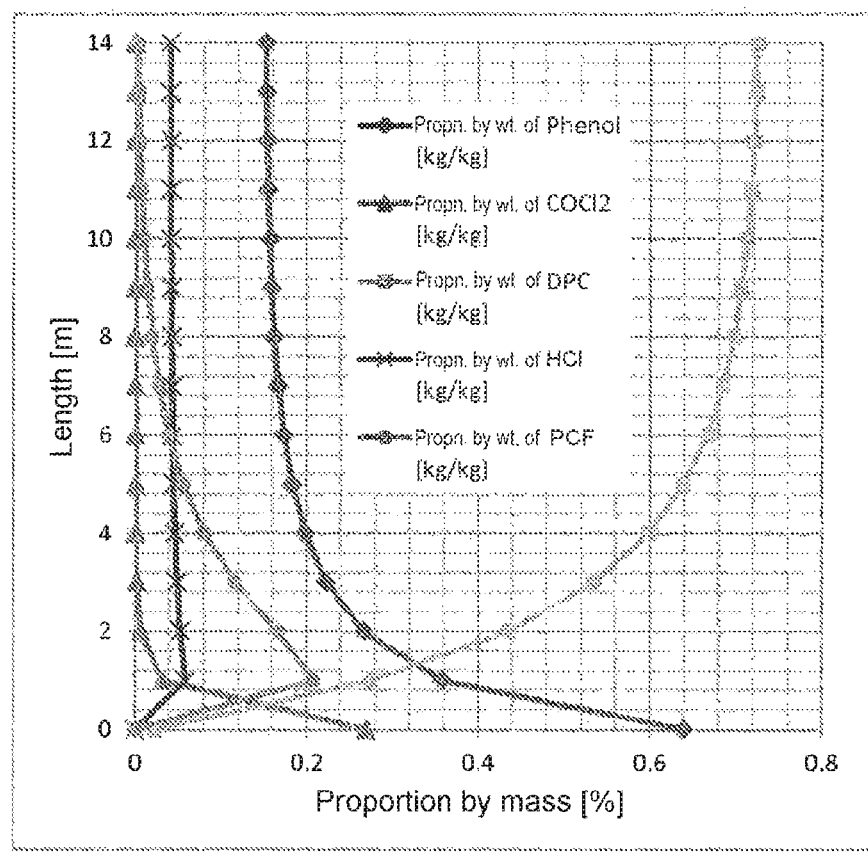

FIG. 4: Concentration profiles of the liquid phase in the reactor

FIG. 5: Graph of the phosgene conversion using the phosgene concentration at the reactor outlet

EXAMPLES

A phenol-, catalyst- and phosgene-containing stream in the composition according to table 1 is fed at a temperature of 170° C. into a bubble column reactor having a length of 14 m. The reaction conditions are adjusted in each case so as to obtain various G/A ratios. At the same time, the phosgene concentrations present at the reactor outlet in the liquid phase are ascertained. The plot of the concentrations (proportions by mass) over the length of the reactor at a G/A ratio of 0.00896 m/s is shown in FIG. 4. FIG. 5 shows the effect of a distinct reduction in the phosgene content at the reactor outlet as a function of the G/A ratio. From a G/A ratio of less than 0.010, there is another distinct increase in the decrease in the amount of phosgene in the liquid phase at the reactor outlet.

TABLE 1

| T | ° C. | 1700.0 | |
|---|---|---|---|
| Total mass | kg/h | 37141.3 | |
| PHENOL | kg/h \| % | 23756.9 | 64.0 |
| COCl$_2$ | kg/h \| % | 9987.8 | 26.9 |
| DPC | kg/h \| % | 832.3 | 2.2 |
| Ti(OPh)$_4$ | kg/h \| % | 1700.0 | 4.6 |
| SALIPHES | kg/h \| % | 657.2 | 1.8 |
| Total volume | m3/h | 37.7 | |

TABLE 2

| Example | Superficial velocity G/A [m/s] | Phosgene concentration Middle of reactor length mg/kg | Phosgene concentration Reactor outlet mg/kg |
|---|---|---|---|
| 1* | 0.288 | 1238.7 | 418.7 |
| 2* | 0.164 | 1085.1 | 302.8 |
| 3* | 0.087 | 703.6 | 107.9 |
| 4* | 0.033 | 193.5 | 5.2 |
| 5 | 0.009 | 24.0 | 0.042 |
| 6 | 0.001 | 8.6 | 0.004 |

*comparative example

The invention claimed is:

1. A process for preparing diaryl carbonate by reaction of an aromatic hydroxyl compound and a halogenated carbonyl in the presence of a catalyst in a reactor, wherein the halogenated carbonyl is passed into the reactor dissolved or in the liquid phase and wherein the ratio G/A is less than 0.010, where G is the entry volume flow rate of the liquid or dissolved halogenated carbonyl in m$^3$/s and A is the internal cross-sectional area orthogonal to the longitudinal axis in m$^2$, and wherein the reactor is at least one bubble column reactor.

2. The process as claimed in claim 1, wherein the reaction takes place in a bubble column reactor in the absence of a solvent.

3. The process as claimed in claim 1, wherein G/A is in the range from 0.0005 [m/s] and 0.0095 [m/s].

4. The process as claimed in claim 1, wherein the ratio H/D is greater than or equal to 2 and H is the height of the liquid phase in the reactor in the gas-free state and D is the diameter of the reactor.

5. The process as claimed in claim 1, wherein the residence time in the reactor is in the range from 0.5 to 4 hours, the temperature is in the range from 120 to 220° C. and the pressure is 3 to 100 bar.

6. The process as claimed in claim 1, wherein the halogenated carbonyl is phosgene.

7. The process as claimed in claim 1, wherein the aromatic hydroxyl compound is phenol.

8. The process as claimed in claim 1, wherein the catalyst is pyridine, pyridine*HCl, TiCl$_4$, Ti(OPh)$_4$ or AlCl$_3$.

9. The process as claimed in claim 1, wherein the process is conducted in at least two stages.

10. The process as claimed in claim 1, wherein the reactor contains a liquid phase and an outlet in the liquid phase, and wherein the phosgene content at the reactor outlet in the liquid phase is less than 100 ppm.

* * * * *